(12) United States Patent
Malinge et al.

(10) Patent No.: US 7,425,440 B2
(45) Date of Patent: Sep. 16, 2008

(54) CULTURE FLASK

(75) Inventors: David S Malinge, Hertfordshire (GB); Richard Wales, St. Neots (GB); Peter Esser, Roskilde (DK); Stephen Guy, Hertfordshire (GB)

(73) Assignee: The Automation Partnership (Cambridge) Limited, Hertfordshire (GB)

( * ) Notice: Subject to any disclaimer, the term of this patent is extended or adjusted under 35 U.S.C. 154(b) by 198 days.

(21) Appl. No.: 10/863,517

(22) Filed: Jun. 9, 2004

(65) Prior Publication Data

US 2004/0259242 A1  Dec. 23, 2004

(30) Foreign Application Priority Data

Jun. 10, 2003  (EP) .................. 03253653

(51) Int. Cl.
| | |
|---|---|
| C12M 1/00 | (2006.01) |
| C12M 1/22 | (2006.01) |
| C12M 1/24 | (2006.01) |
| C12M 1/34 | (2006.01) |
| C12M 3/00 | (2006.01) |
| C12N 1/00 | (2006.01) |
| C12N 1/12 | (2006.01) |
| C12N 1/20 | (2006.01) |
| C12N 5/00 | (2006.01) |
| C12N 5/02 | (2006.01) |

(52) U.S. Cl. .................. 435/288.1; 435/243; 435/252.1; 435/252.4; 435/254.1; 435/325; 435/410; 435/283.1; 435/288.2; 435/304.1; 435/304.2; 435/304.3; 435/305.1; 435/305.2; 435/307.1

(58) Field of Classification Search ....................... None
See application file for complete search history.

(56) References Cited

U.S. PATENT DOCUMENTS

| | | | |
|---|---|---|---|
| 3,589,983 | A | 6/1971 | Holderith et al. |
| 4,121,976 | A | 10/1978 | Gleeson |
| 5,310,676 | A | 5/1994 | Johansson et al. |
| 2001/0055803 | A1 | 12/2001 | Wall et al. |

FOREIGN PATENT DOCUMENTS

| | | |
|---|---|---|
| EP | 0 743 362 | 11/1996 |
| FR | 2 631 633 | 11/1989 |

*Primary Examiner*—David M. Naff
*Assistant Examiner*—Deborah K. Ware

(57) ABSTRACT

A culture flask 10 comprises two or more internal chambers 18-21 defining a plurality of parallel surfaces of different sizes and means for fluid communication 24 between the chambers 18-20.

3 Claims, 6 Drawing Sheets

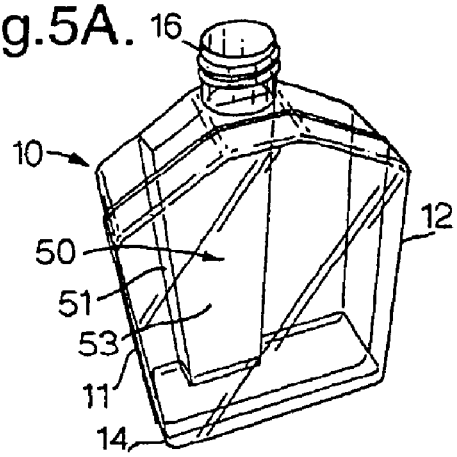
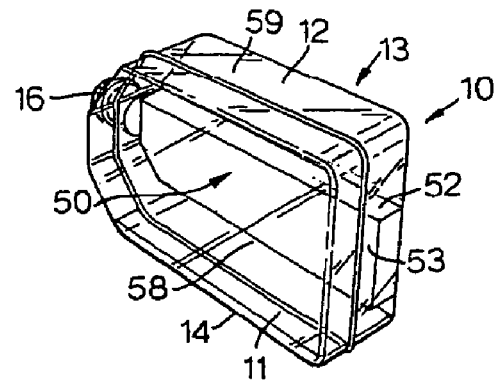
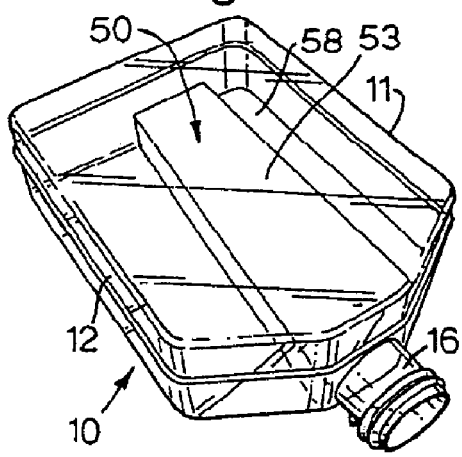
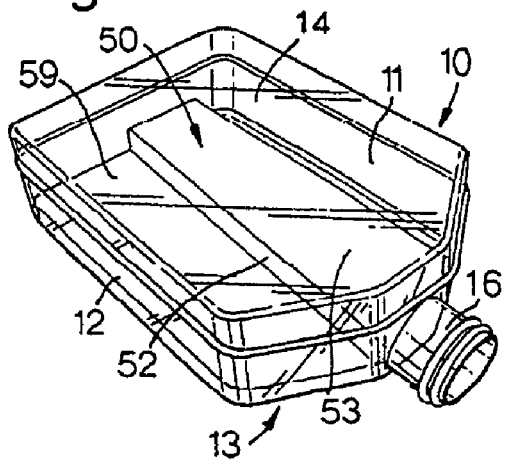
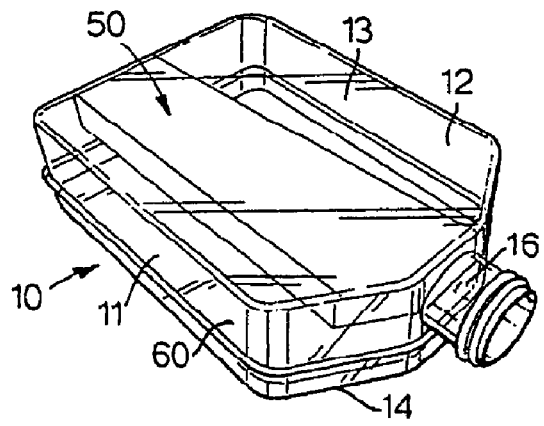
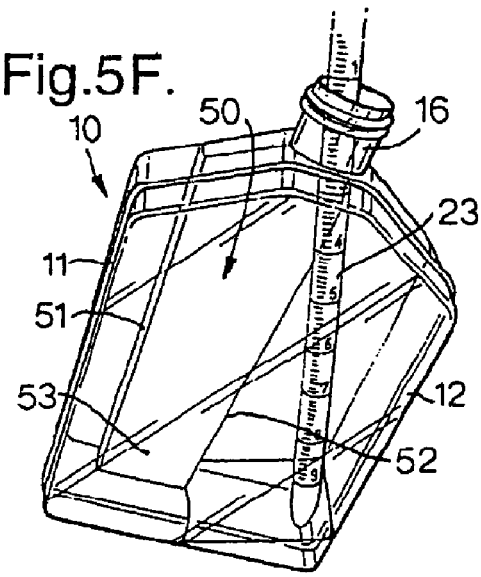

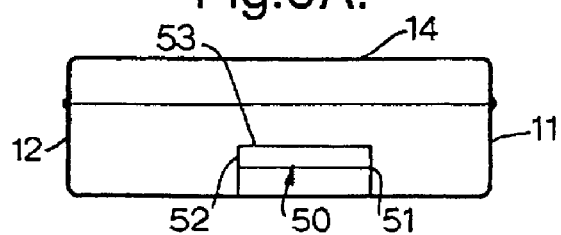
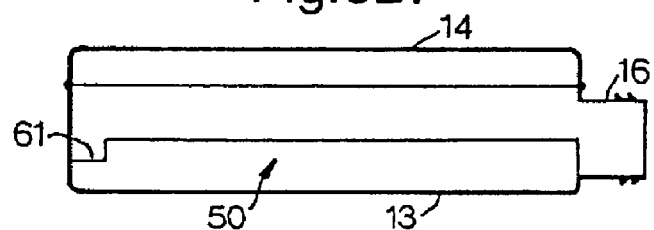
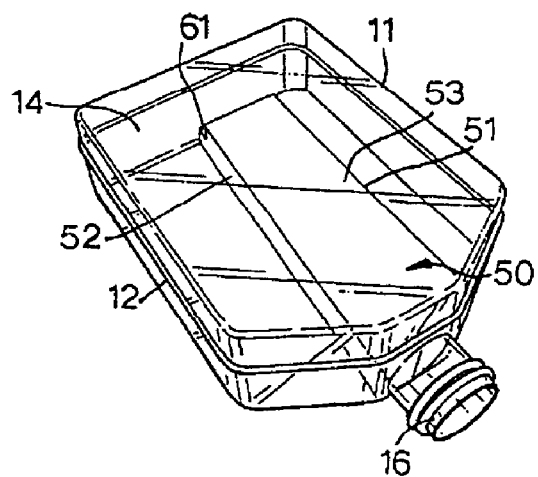
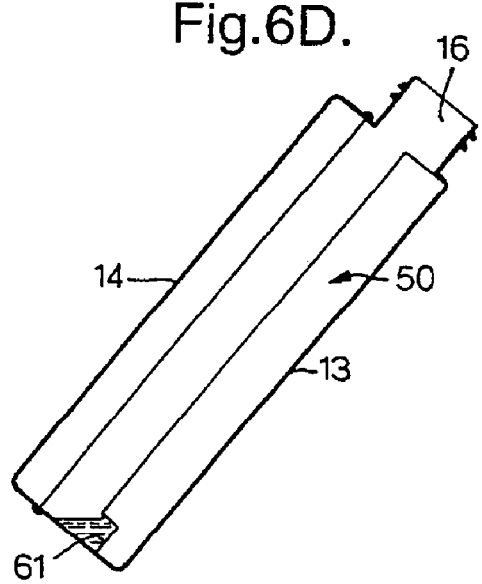

CULTURE FLASK

BACKGROUND OF THE INVENTION

The present invention relates to a cell culture flask.

It is common, within the field of cell biology, to culture cells in order to harvest biologically active compounds produced by the cells, or indeed the cells themselves. Such cells are generally cultured on static plates which may be enclosed in a bottle or flask or on a plate with a cooperating lid. Flasks may generally be accessed through a neck portion, closed by means of a cap. Plates are accessed by the removal of a lid portion. Both flasks and plates are , in use, laid on their side, so that the maximum possible surface are a is horizontal. The cell cultivating medium covers the inner surface area of the flask wall. Hereafter in this specification plates and flasks are collectively referred to as flasks. Over time, the industry has developed a number of sizes of flask that are considered to be standard. One of these, known as the T-flask, has four orthogonal walls (two major walls and two minor walls) and is configured so that the maximum surface are a is available to the cells when the flask is laid on one of its major sides.

In order to make maximum use of the volume enclosed by such a flask it has been suggested that the flask could be divided by a number of internal walls. For example, U.S. Pat. No. 5,310,676 discloses a cell culturing flask comprising superposed, separate partition wall members forming mutually spaced partition walls, which define three superposed chambers for containing a cell cultivating medium therebetween. The superposed partition wall members each comprise a partition wall and an upstanding peripheral wall extending transversely thereto in order to provide a fluid passage which allows the cell culture to be distributed between the various levels within the device.

It is also known within the art that certain cell cultures will only thrive between certain concentration limits. If the concentration of cells and cell culture medium is too low, ie the are a on which the cell culture medium is isolated is too large, then the cells will not thrive. Conversely, when the cell population increases beyond a certain level further growth cannot be sustained within the limits of the are a on which the cells are isolated. Therefore, it would be advantageous for the cells to be moved from one surface to a second larger surface and possibly subsequent further larger surfaces within the culture flask during the culturing process in order to maximise culture growth without decanting the medium cell suspension from one flask into one or more others.

SUMMARY OF THE INVENTION

According to the present invention there is, therefore, provided a culture flask comprising two or more internal chambers defining a plurality of parallel surfaces of different sizes and a fluid passage for fluid communication between the chambers.

Preferably, the internal chambers are configured such that an access port is included to enable a pipette to access each of the chambers and the configuration of the chambers is such that each chamber can be used sequentially.

Furthermore, according to the present invention, there is provided a method of culturing cells within a flask that is provided with a series of internal chambers defining a plurality of parallel surfaces of different sizes, the method comprising the steps of putting cells in a suspension of growing medium into the smallest chamber, pipetting out a sample of cells to determine the cell concentration, turning or inverting the flask to allow the cells to move into a second, larger, chamber. The method may further include repeating the pipetting and turning or inverting of the flask to allow the cells to move into a further, larger chamber.

BRIEF DESCRIPTION OF THE DRAWINGS

A number of examples of the present invention will now be further described with reference to the accompanying drawings, in which:

FIGS. 5a to 5f show another example of the present invention from various angles.

FIGS. 6a to 6d show another embodiment of the invention.

DETAILED DESCRIPTION OF THE DRAWINGS

Figure 1:
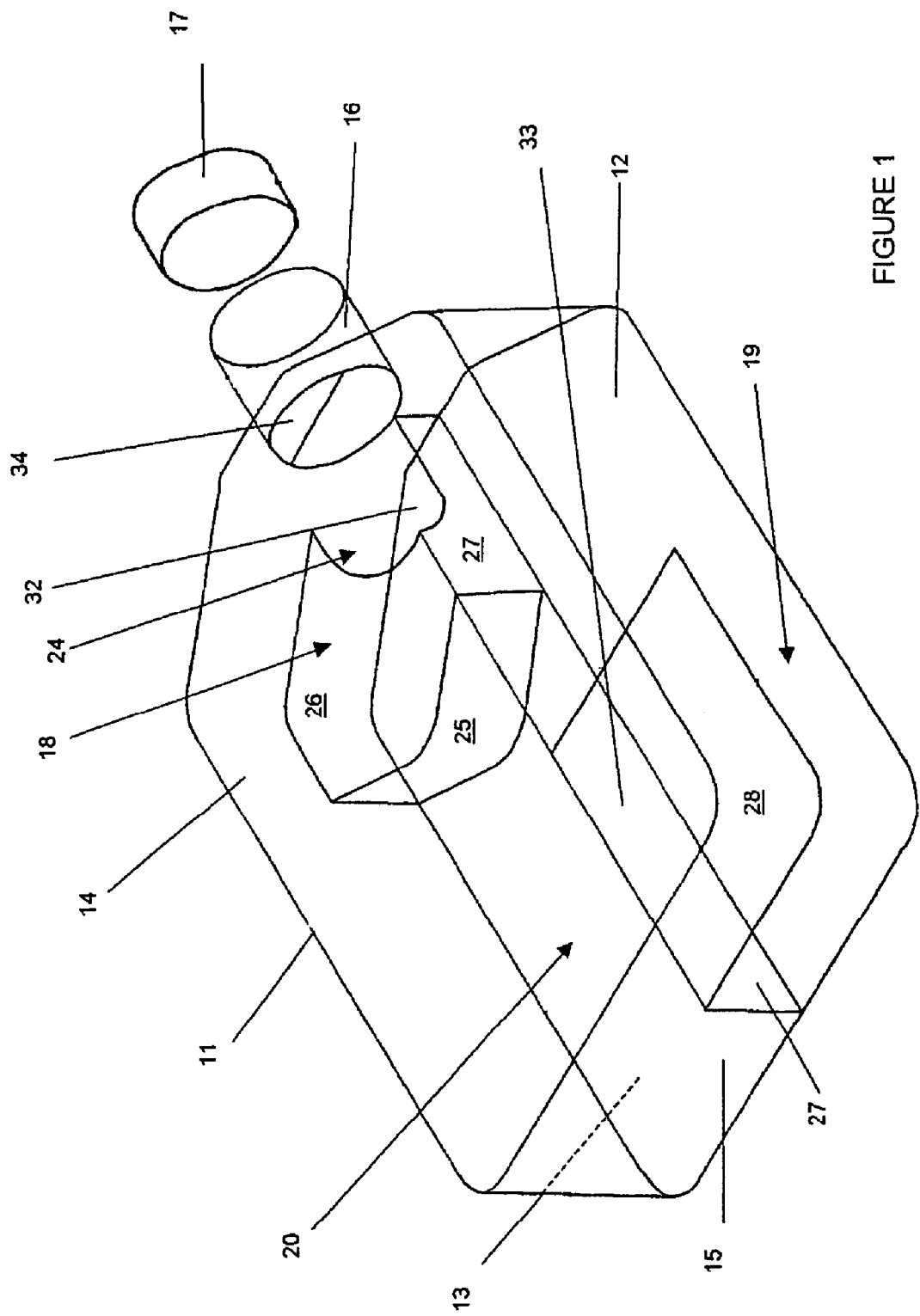
FIG. 1 is a perspective view of one example of the invention.

FIG. 1 shows a first example a culture flask 10 according to the present invention. The flask 10 is constructed with four orthogonal walls 11, 12, 13 and 14 and abase 15. There are two major walls 13, 14 and two minor walls 11, 12. Above the four orthogonal walls 11-14 the walls of the flask 10 converge to meet at a neck portion 16. The neck 16 is screw threaded and co-operates, in use, with a cap 17 to seal the contents of the flask from the ambient atmosphere. In use, the flask is placed on either of the major walls 13, 14.

The culture flask 10 is divided into a number of internal chambers 18-20 by use of various dividing walls 25-28 defining, together with the minor walls 11, 12, chambers 18, 19 and 20 to be of different sizes. When the flask 10 is first in use, that is lying on the major wall 13, the surface are a presented in chamber 18 is considerably smaller than that of chamber 19. Chamber 20 (see FIG. 3) corresponds to the are a of the wall 14 of the T-flask and is therefore larger than either chamber 18 or chamber 19. Cells are initially cultured within chamber 18. As time passes and the cell concentration changes, it is advantageous to be able to monitor the cell concentration by pipetting of a small sample from the chamber 18. The chambers are configured such that this is possible accessing the flask 10 via the neck 16. The dividing walls 25 to 28 of the flask ensure that a pipette 23 can access all of the chambers 18, 19, 20 (see FIG. 4). When the cell concentration is deemed to be sufficient for further culturing of the cells within chamber 18 to be impractical the cells are transferred to the larger chamber 19 via part of a fluid passageway 24 or by using a pipette 23 to transfer the contents from chamber 18 to the larger chamber 19.

The fluid passageway 24 consists of a number of sections of the internal walls 25-28 that have gaps to allow the cells and the culture medium to move from one chamber to another when the flask 10 is held at a suitable angle. In the example shown in FIG. 1, the cells suspended in a culture medium enter the flask 10 through the neck 16 and are localised in the smallest chamber 18. The cells are then grown with the flask 10 feeding off the culture medium with the flask 10 in the position shown in FIG. 1 with major wall 14 uppermost. After the cells have been growing for some time and feeding on the culture medium, they may run out of medium and more can be supplied directly to the chamber in which the cells are growing. The fluid passageway 24 from chamber 18 to chamber 19 consists of a gap 32 between the internal walls 26, 27 and the major wall 14. When the cells require more space and also more culture medium, it is necessary to move them into a larger chamber. In order to move the cells it is first necessary to detach them from the surface of the chamber on which they have been growing and move the cells to a second chamber 19 and then to add more culture medium. The cells are detached from the surface using an enzyme such as trypsin. In addition it may be necessary to shake the flask to aid the removal of the cells from the surface 13. The addition of the medium after the movement of the cells into a new chamber dilutes the trypsin which would otherwise prevent the cells from adhering to the surface. The flask 10 is held at an angle to allow the contents of chamber 18 to drain into chamber 19. The flask 10 is then allowed to rest with major wall 14 uppermost again and the cells adhere to the inner surface of the wall 13 in chamber 19 and continue to grow. The fluid passageway 24 from chamber 19 to chamber 20 consists of a gap 33 between sections of the internal walls 27 and the major wall 14. The process of detaching the cells, adding new medium and moving the resulting suspension to a larger chamber are then repeated to move the cells into chamber 20 with the flask now resting on major wall 14, wall 13 uppermost. In order to prevent the cell suspension from flowing out through the neck portion 16 of the flask 10 there is a dam 34 to contain the suspension. The cells grow on the major wall 14, thus providing a larger surface that is completely new, on which the cells can grow.

Figure 2:
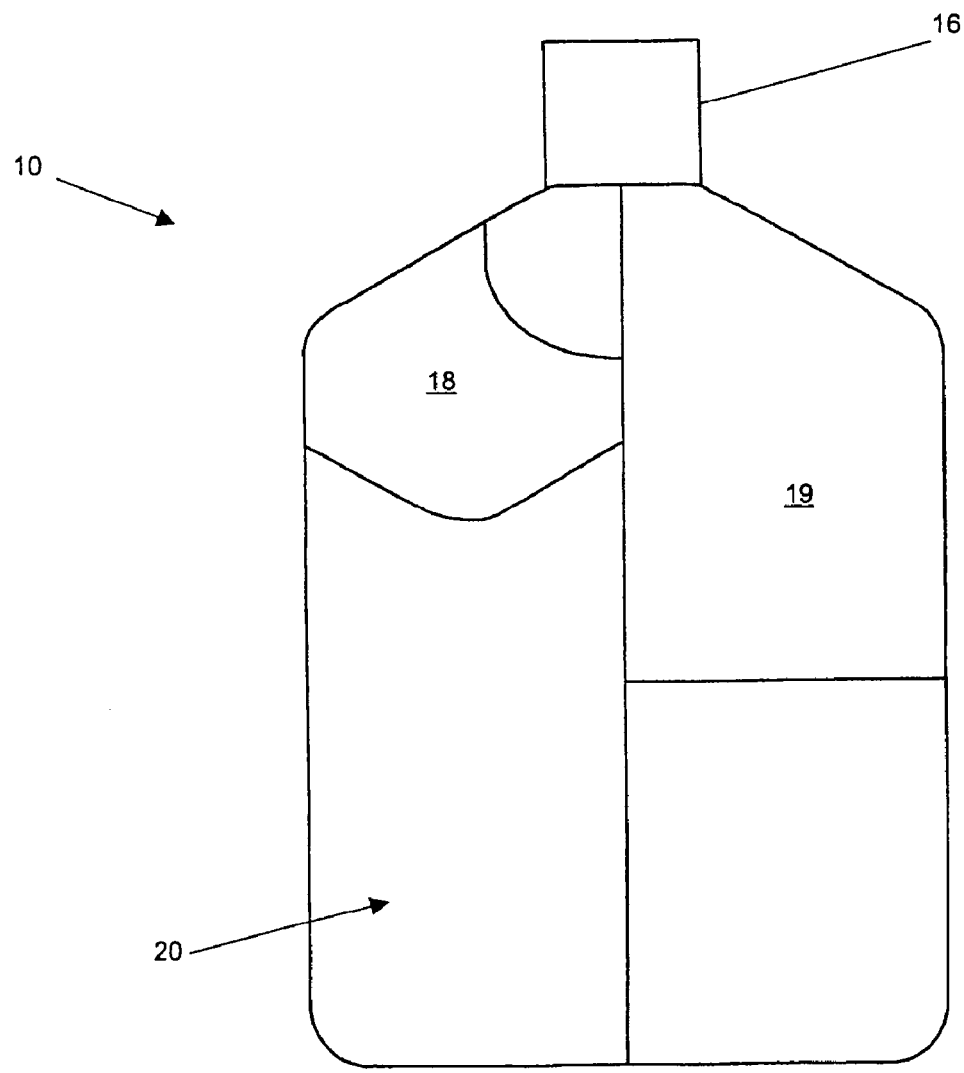
FIG. 2 is a plan view of the example shown in FIG. 1.

FIG. 2 shows a plan view of the flask 10 showing the relative sizes of the chambers 18, 19 and 20.

Figure 3:
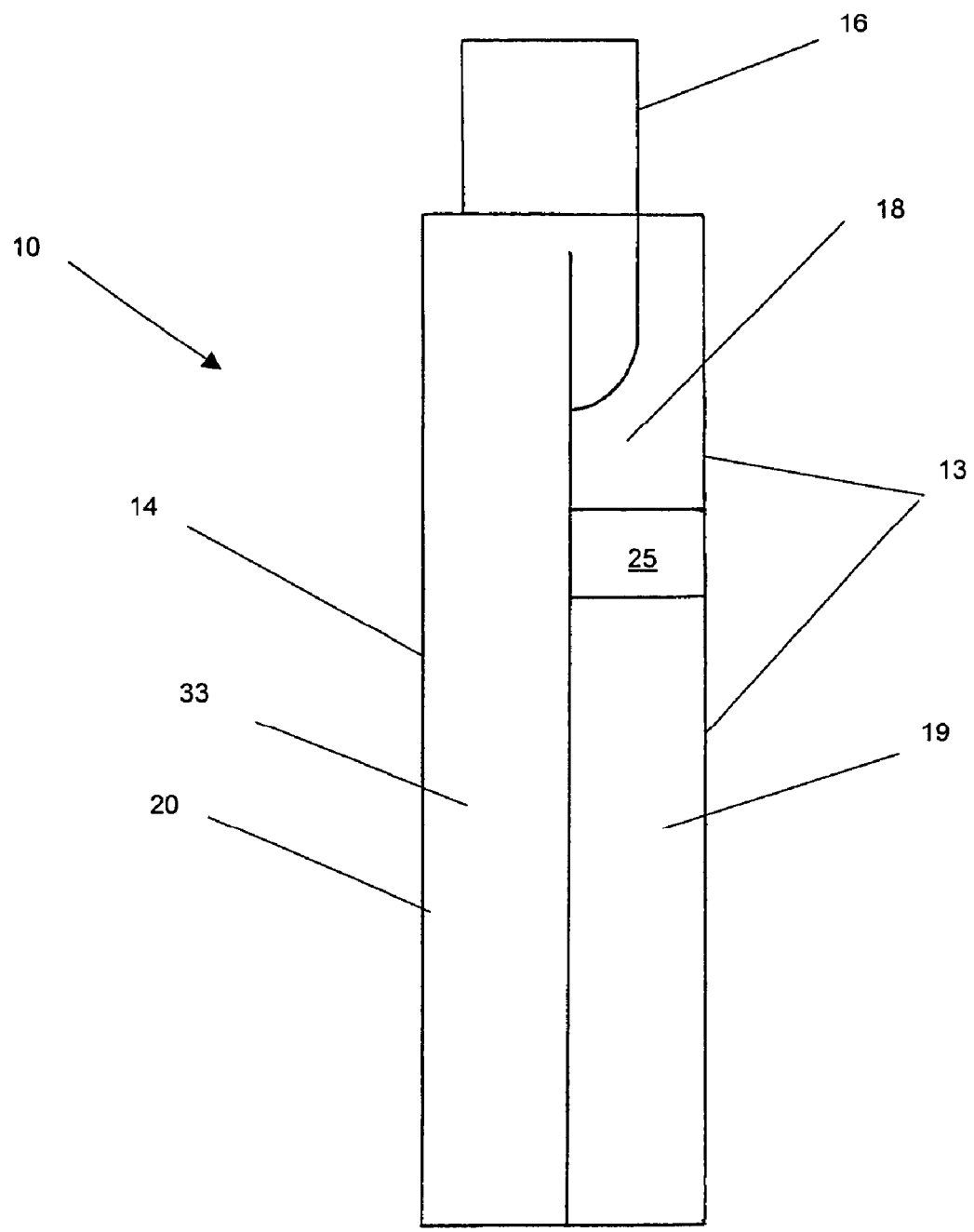
FIG. 3 is a view of the example shown in FIG. 1 from the side.

FIG. 3 shows a side view of the flask 10 through the minor wall 12. This shows the configuration of the chambers 18, 19 and 20.

Figure 4:
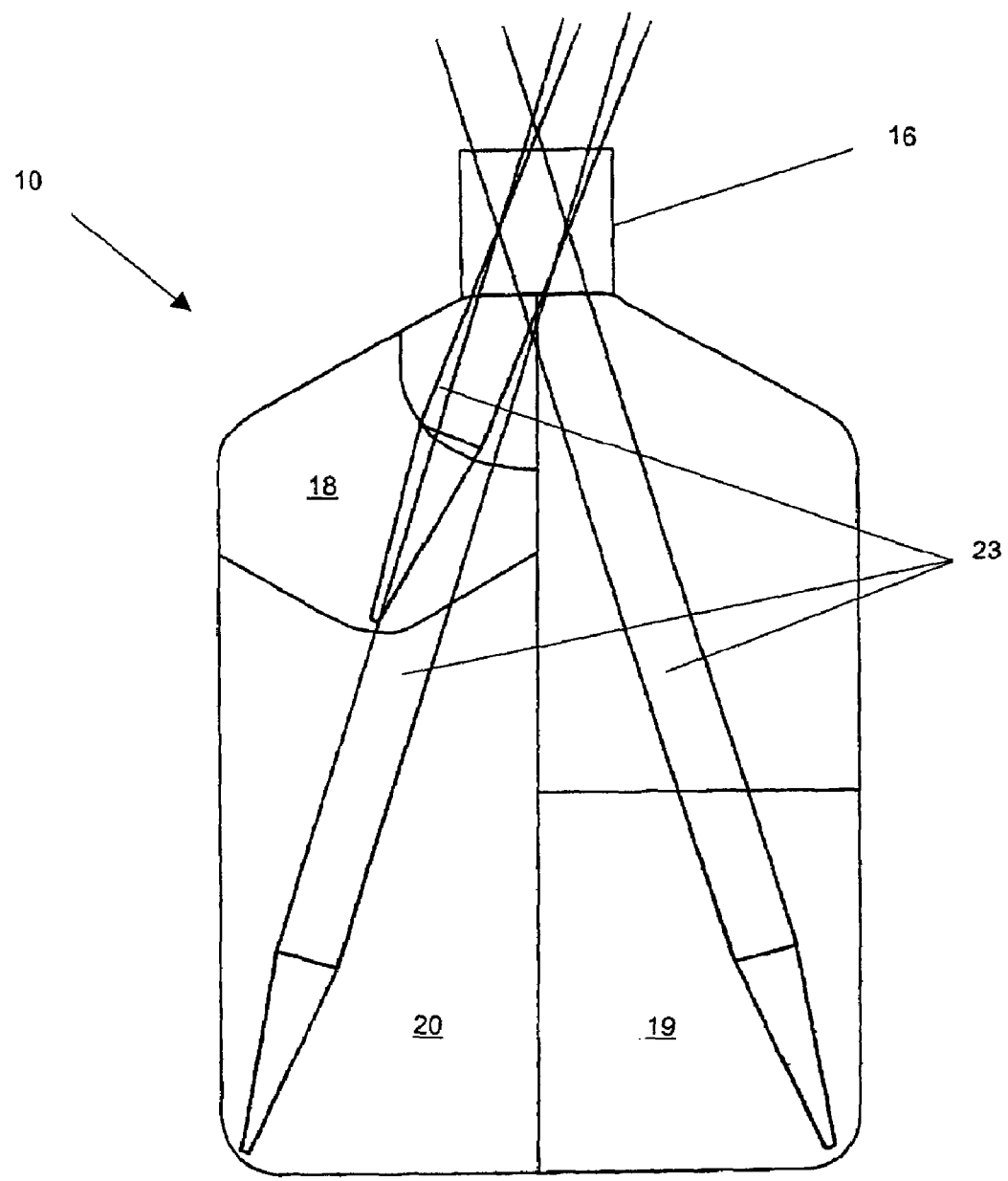
FIG. 4 shows an example of one embodiment of the invention in use.

FIG. 4 shows a pipette 23 inserted into the culture flask 10 to remove a small sample of cell suspension for determining the cell concentration within the culture flask 10 or to transfer cells and medium from chamber 18 to chamber 19 and so on until it is transferred into chamber 20. The pipette 23 is capable of accessing each of the chambers 18, 19, 20 to extract a sample.

FIGS. 5a to 5f show various views of a second example of a flask according to the present invention. In this example there is provided a block 50 made from two minor walls 51 and 52 that lie substantially parallel to the minor walls 11, 12 of the flask 10; a major wall 53 parallel to the major walls 13, 14 of the flask 10 and part of major wall 13. This block 50 serves the same purpose as the internal walls 26, 27 of the flask 10 of the first example shown in FIGS. 1 to 4, namely they divide the area in which cells are cultured into a number of distinct and differently sized chambers 58, 59, 60. The depth of the block 50 is less than the total depth of the flask 10. Therefore the major wall 14 is uninhibited and therefore is available in its entirety for the culture of cells. In use, cells are cultured in one of the chambers and then, when they require more space for growth they are moved into a larger chamber. Once cells have been cultured in one of the smaller chambers the chamber is not reused.

FIG. 5a shows the filling position with the flask 10 standing on its base. The flask 10 can then be filled through the neck with a suspension containing the cells to be cultured suspended in a medium of culture medium on which the cells will feed as they grow. The flask 10 is then rested on the minor wall 12 in order to distribute the cells and medium to the correct side of the flask 10 as shown in FIG. 5b. The flask is then tipped to lie on major wall 13 and the cells and medium move into chamber 58 as shown in FIG. 5c. The cells are then cultured sequentially in chambers 59 and 60 as shown in FIGS. 5d and e respectively. In this example the ratio of are as between the three chambers is 1:3:7, but other ratios are contemplated.

As described above the depth of the block 50 is less than the depth of the flask 10. Not only does this allow cells to be cultured across the entirety of the inner surface of the major wall 14 but also it allows a pipette 23 to access all parts of the flask 10 that are used for culturing cells.

FIG. 6 shows a modification of the second example shown in FIG. 5. FIG. 6a shows a view through the base 15 of the flask 10 and FIG. 6b shows a view through the minor wall 12. In this example there is provided, through the block 50, a channel 61 along which the cells and cell culture medium can flow when they are to be moved from chamber 58 to chamber 59. The channel lies adjacent the base 15 of the flask 10. It is approximately one third of the depth of the block 50 so that when the flask 10 is lying on major wall 13, as shown in FIG. 6c, and the cells are being cultured in either chamber 58 or 59 there is no possibility of the cells escaping into the other chamber. When the cells are moved from chamber 58 to chamber 59, as shown in FIG. 6d, the provision of the channel 61 reduces the proportion of the block 50 that is covered with the cells and medium during the transfer between chambers and therefore reduces the wastage and possible subsequent contamination of chamber 59 with matter falling from the major wall 53 of the block 50.

The provision of a number of different chambers 18 to 20 or 58 to 60 ensures that as the cells and their culture medium are moved from one chamber to another the surfaces are not reused. The surfaces may be pre-treated with an agent that facilitates adhesion of the cells to the surface and the practice of reusing are as may result in the advantages associated with this pre-treatment being lost.

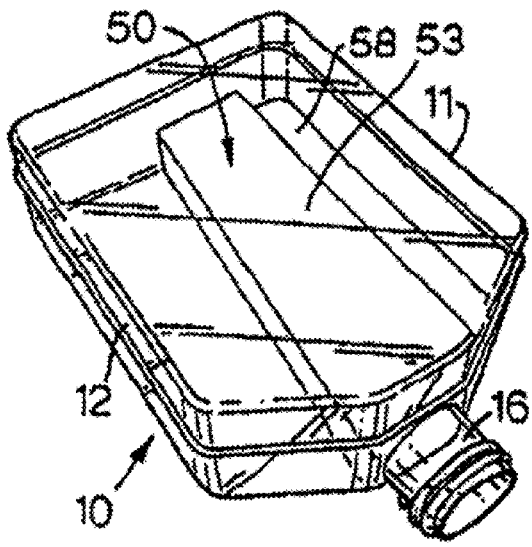

The invention claimed is:

1. A culture flask comprising:
a single chamber containing two or more internal chambers of different sizes, said single chamber, defined by two spaced apart parallel major walls joined together by two spaced apart minor parallel walls and a base wall joining together the two major walls and minor walls, said major and minor walls converging from the base wall to form a neck portion having an access port providing access to each of said two or more internal chambers for introduction of cells and culture medium, said two or more internal chambers being defined by at least one internal dividing wall extending partially from one major wall towards the other major wall such that when the flask is lying on the major wall from which the at least one internal dividing wall extends, first and second said internal chambers of different sizes are provided, and when the flask is lying on the opposite major wall, a third said internal chamber is provided that is not divided by the at least one internal dividing wall, and between said first and second internal chambers of different sizes a channel exists for transfer of cells and culture medium from one of said first and second internal chambers to the larger of said first and second internal chambers by the flask being held at a suitable angle.

2. A culture flask according to claim 1, wherein the neck portion of the flask is closable.

3. A culture flask according to claim 1, wherein the flask has three internal chambers having areas in a ratio of 1:2:4.

* * * * *

UNITED STATES PATENT AND TRADEMARK OFFICE
CERTIFICATE OF CORRECTION

PATENT NO. : 7,425,440 B2
APPLICATION NO. : 10/863517
DATED : September 16, 2008
INVENTOR(S) : Malinger et al.

It is certified that error appears in the above-identified patent and that said Letters Patent is hereby corrected as shown below:

Delete present Title page, and substitute therefor, new Title page illustrating a figure. (attached)

Signed and Sealed this

Eighteenth Day of November, 2008

JON W. DUDAS
*Director of the United States Patent and Trademark Office*

United States Patent
Malinge et al.

(10) Patent No.: US 7,425,440 B2
(45) Date of Patent: Sep. 16, 2008

(54) CULTURE FLASK

(75) Inventors: David S Malinge, Hertfordshire (GB); Richard Wales, St. Neots (GB); Peter Esser, Roskilde (DK); Stephen Guy, Hertfordshire (GB)

(73) Assignee: The Automation Partnership (Cambridge) Limited, Hertfordshire (GB)

(*) Notice: Subject to any disclaimer, the term of this patent is extended or adjusted under 35 U.S.C. 154(b) by 198 days.

(21) Appl. No.: 10/863,517

(22) Filed: Jun. 9, 2004

(65) Prior Publication Data
US 2004/0259242 A1   Dec. 23, 2004

(30) Foreign Application Priority Data
Jun. 10, 2003   (EP) .................. 03253653

(51) Int. Cl.
*C12M 1/00* (2006.01)
*C12M 1/22* (2006.01)
*C12M 1/24* (2006.01)
*C12M 1/34* (2006.01)
*C12M 3/00* (2006.01)
*C12N 1/00* (2006.01)
*C12N 1/12* (2006.01)
*C12N 1/20* (2006.01)
*C12N 5/00* (2006.01)
*C12N 5/02* (2006.01)

(52) U.S. Cl. .......... 435/288.1; 435/243; 435/252.1; 435/252.4; 435/254.1; 435/325; 435/410; 435/283.1; 435/288.2; 435/304.1; 435/304.2; 435/304.3; 435/305.1; 435/305.2; 435/307.1

(58) Field of Classification Search .......... None
See application file for complete search history.

(56) References Cited

U.S. PATENT DOCUMENTS

| | | | |
|---|---|---|---|
| 3,589,983 A | 6/1971 | Holderith et al. |
| 4,121,976 A | 10/1978 | Gleeson |
| 5,310,676 A | 5/1994 | Johansson et al. |
| 2001/0055803 A1 | 12/2001 | Wall et al |

FOREIGN PATENT DOCUMENTS

| | | |
|---|---|---|
| EP | 0 743 362 | 11/1996 |
| FR | 2 631 633 | 11/1989 |

*Primary Examiner*—David M. Naff
*Assistant Examiner*—Deborah K. Ware

(57) ABSTRACT

A culture flask 10 comprises two or more internal chambers 18-21 defining a plurality of parallel surfaces of different sizes and means for fluid communication 24 between the chambers 18-20.

3 Claims, 6 Drawing Sheets

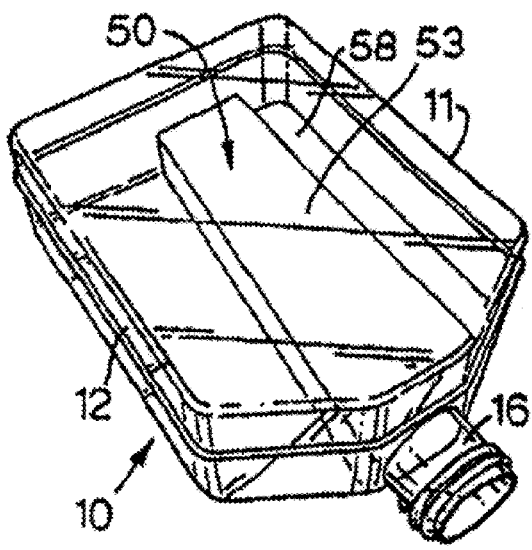

UNITED STATES PATENT AND TRADEMARK OFFICE
CERTIFICATE OF CORRECTION

| | |
|---|---|
| PATENT NO. | : 7,425,440 B2 |
| APPLICATION NO. | : 10/863517 |
| DATED | : September 16, 2008 |
| INVENTOR(S) | : Malinge et al. |

It is certified that error appears in the above-identified patent and that said Letters Patent is hereby corrected as shown below:

Delete present Title page, and substitute therefor, new Title page illustrating a figure. (attached)

This certificate supersedes the Certificate of Correction issued November 18, 2008.

Signed and Sealed this

Ninth Day of December, 2008

JON W. DUDAS
*Director of the United States Patent and Trademark Office*

United States Patent
Malinge et al.

(10) Patent No.: US 7,425,440 B2
(45) Date of Patent: Sep. 16, 2008

(54) CULTURE FLASK

(75) Inventors: David S Malinge, Hertfordshire (GB); Richard Wales, St. Neots (GB); Peter Esser, Roskilde (DK); Stephen Guy, Hertfordshire (GB)

(73) Assignee: The Automation Partnership (Cambridge) Limited, Hertfordshire (GB)

(*) Notice: Subject to any disclaimer, the term of this patent is extended or adjusted under 35 U.S.C. 154(b) by 198 days.

(21) Appl. No.: 10/863,517

(22) Filed: Jun. 9, 2004

(65) Prior Publication Data

US 2004/0259242 A1 Dec. 23, 2004

(30) Foreign Application Priority Data

Jun. 10, 2003 (EP) ............... 03253633

(51) Int. Cl.
C12M 1/00 (2006.01)
C12M 1/22 (2006.01)
C12M 1/24 (2006.01)
C12M 1/34 (2006.01)
C12M 3/00 (2006.01)
C12N 1/00 (2006.01)
C12N 1/12 (2006.01)
C12N 1/20 (2006.01)
C12N 5/00 (2006.01)
C12N 5/02 (2006.01)

(52) U.S. Cl. ............. 435/288.1; 435/243; 435/252.1; 435/252.4; 435/254.1; 435/325; 435/410; 435/283.1; 435/288.2; 435/304.1; 435/304.2; 435/304.3; 435/305.1; 435/305.2; 435/307.1

(58) Field of Classification Search ............... None
See application file for complete search history.

(56) References Cited

U.S. PATENT DOCUMENTS

| | | |
|---|---|---|
| 3,589,983 A | 6/1971 | Holderith et al. |
| 4,121,976 A | 10/1978 | Gleeson |
| 5,310,676 A | 5/1994 | Johansson et al. |
| 2001/0055803 A1 | 12/2001 | Wall et al |

FOREIGN PATENT DOCUMENTS

| | | |
|---|---|---|
| EP | 0 743 362 | 11/1996 |
| FR | 2 631 633 | 11/1989 |

*Primary Examiner*—David M. Naff
*Assistant Examiner*—Deborah K. Ware

(57) ABSTRACT

A culture flask 10 comprises two or more internal chambers 18-21 defining a plurality of parallel surfaces of different sizes and means for fluid communication 24 between the chambers 18-20.

3 Claims, 6 Drawing Sheets